United States Patent
Grace et al.

(10) Patent No.: US 6,801,677 B1
(45) Date of Patent: Oct. 5, 2004

(54) WAVEGUIDE-BASED OPTICAL CHEMICAL SENSOR

(75) Inventors: Karen M. Grace, Ranchos de Taos, NM (US); Basil I. Swanson, Los Alamos, NM (US); Seppo Honkanen, Tucson, AZ (US)

(73) Assignee: The Regents of the Universtiy of California, Los Alamos, NM (US)

( * ) Notice: Subject to any disclaimer, the term of this patent is extended or adjusted under 35 U.S.C. 154(b) by 364 days.

(21) Appl. No.: 10/052,862

(22) Filed: Nov. 9, 2001

Related U.S. Application Data (63) Continuation-in-part of application No. 09/393,543, filed on Sep. 10, 1999, now abandoned.
(60) Provisional application No. 60/100,250, filed on Sep. 10, 1998.

(51) Int. Cl.[7] .................................................. G02B 6/12
(52) U.S. Cl. ............................ 385/12; 385/11; 385/14; 385/15; 385/16
(58) Field of Search ............................. 385/12, 10–11, 385/14–16, 147

(56) References Cited

U.S. PATENT DOCUMENTS

| | | | | |
|---|---|---|---|---|
| 3,988,704 A | * | 10/1976 | Rice et al. | 359/250 |
| 5,418,058 A | * | 5/1995 | Li et al. | 428/327 |
| 5,422,713 A | * | 6/1995 | Bramson | 356/73.1 |
| 5,687,721 A | * | 11/1997 | Kuhls | 600/316 |
| 5,923,795 A | * | 7/1999 | Toyohara | 385/11 |
| 5,946,097 A | * | 8/1999 | Sanders et al. | 356/464 |
| 6,222,951 B1 | * | 4/2001 | Huang | 385/14 |

* cited by examiner

*Primary Examiner*—Mohammad Sikder
(74) *Attorney, Agent, or Firm*—Gemma Morrison Bennett; Samuel L. Borkowsky (57) ABSTRACT

The invention provides an apparatus and method for highly selective and sensitive chemical sensing. Two modes of laser light are transmitted through a waveguide, refracted by a thin film host reagent coating on the waveguide, and analyzed in a phase sensitive detector for changes in effective refractive index. Sensor specificity is based on the particular species selective thin films of host reagents which are attached to the surface of the planar optical waveguide. The thin film of host reagents refracts laser light at different refractive indices according to what species are forming inclusion complexes with the host reagents.

21 Claims, 10 Drawing Sheets

Fig. 10 ically oriented modes of laser light having a small difference in frequency are transmitted through a planar optical waveguide, into a polarization analyzer and thence into a photodetector such as a photodiode or photomultiplier. The signal from the photodetector is compared with a reference signal from the laser in a phase sensitive detector.

WAVEGUIDE-BASED OPTICAL CHEMICAL SENSOR

This application claims the benefit of U.S. Provisional Application No. 60/100,250, filed Sep. 10, 1998, and is a Continuation in Part of application Ser. No. 09/393,543 filed Sep. 10, 1999, now abandoned.

TECHNICAL FIELD

This invention relates to detection of specific chemical substances using species selective thin films, planar optical waveguides and laser interferometry.

This invention was made with government support under Contract No. W-7405-ENG-36 awarded by the U.S. Department of Energy. The government has certain rights in the invention.

BACKGROUND ART

There is an increasing need for gas sensors which can distinguish extremely low levels of particular gaseous species in the presence of large concentrations of interfering species.

Several fiber optic and integrated optical transducers have been proposed as chemical sensors. Typically, such proposed sensors have been based on a change in the effective refractive index of a guided light mode due to a change in refractive index and/or a change in the thickness of a sensing overlayer. Many such sensors have one or more deficiencies in sensitivity, selectivity, or response time. Thus there is still a need for highly sensitive and selective gas sensors which operate in near real time.

Therefore, it is an object of this invention to provide a method and apparatus for rapid detection of low levels of selected chemical species.

It is another object of this invention to provide a method for sensing chemicals by analysis of changes in the refractive index of a thin film of host reagent on a waveguide caused by the formation of guest-host inclusion complexes in the thin film.

It is yet another object of this invention to provide a method and apparatus for detecting volatile and semi-volatile organic compounds.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims. The claims appended hereto are intended to cover all changes and modifications within the spirit and scope thereof

DISCLOSURE OF INVENTION

Two collinear, orthogonally oriented modes of laser light having a small difference in frequency are transmitted through a planar optical waveguide, into a polarization analyzer and thence into a photodetector such as a photodiode or photomultiplier. The signal from the photodetector is compared with a reference signal from the laser in a phase sensitive detector.

Thin films of host reagents comprised of molecules having cavities are covalently bound to the surface of the waveguide. The host reagents form inclusion complexes with targeted molecules to be sensed.

The refractive index of the thin film of host reagent on the optical waveguide changes according to what species, and in what concentrations, are forming inclusion complexes with the host reagent. The molecules of the targeted chemical species are detected by observing the resulting changes of the effective refractive index of the guided light modes propagating through the waveguide.

The apparatus for chemical sensing comprises: (a) a light source to generate a beam of laser light having two modes of laser light with closely spaced frequencies and that are collinear and orthogonally polarized; (b) a species-selective or size-selective thin film of host reagent bonded to the surface of a waveguide into which the laser beam is directed; (c) coupling lenses to couple light into and out of the waveguide; (f) a polarizer to analyze and transmit a portion of the two light modes emitted from the waveguide; (g) a photodetector to detect the beat frequency generated by interference of the collinear orthogonally polarized modes of light coming from the polarizer; (h) a phase sensitive detector device such as a lock-in amplifier to compare the phase of the photodetector output to the phase of a reference signal supplied by the laser light source. A PC is used to read output and collect data.

Because the formation of inclusion complexes is reversible, the sensor apparatus can be used for substantially real-time sensing of chemical agents. Sensor sensitivity can be tuned and choice of chemicals to be detected can be made by varying the size of the host reagent cavities and by selecting the chemical functionality of the host reagent molecules.

Using a plurality (up to hundreds) of ribbed channels in the waveguide can enhance sensitivity and specificity of the sensor, provide a means for concurrent detection of different chemical species, and provide one or more reference channels. Use of more than one host reagent can enable concurrent detection of more than one species.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings.

BEST MODES FOR CARRYING OUT THE INVENTION

A sensor beam consisting of two collinear, orthogonally polarized modes of laser light having a small difference in frequency is produced by a laser or other laser light source. The beam is coupled into a planar optical waveguide. Species selective thin films of host reagents with cavity shaped molecules specifically tailored for optimized and reversible binding of targeted chemicals are covalently bound to the external surface of the waveguide. The host reagents form reversible inclusion complexes with the targeted molecules.

The index of refraction of the species-selective thin film of host reagent varies according to the number and kind of guest-host inclusion complexes formed in the film.

Each of the orthogonal modes of the beam propagating through the waveguide undergoes different changes in effective refractive index due to the formation of guest-host inclusion complexes on the surface of the waveguide. As a result there is phase retardation of one of the modes relative to the other.

The beam emanating from the waveguide is directed through a polarizing analyzer. The transmission axis of the polarizing analyzer is set at 45° with respect to the polarization axis of the two modes.

The two modes are transmitted from the polarizing analyzer to a photodetector such as a photomultiplier or photodiode, where interference between the two modes produces an electrical interference signal having a beat frequency which is the difference between the frequencies of the two modes. The intensity of the light reaching the photodetector can be described as:

where I = intensity of the beam
$A_1$ = the amplitude of the first mode
$A_2$ = the amplitude of the second mode
$k_1$ = wave number of the first mode
$k_2$ = wave number of the second mode
L = length of the waveguide
$\omega_1$ = angular frequency of the first mode
$\omega_2$ = angular frequency of the second mode
$(\omega_1 - \omega_2)$ = beat frequency of the beam
t = time In this formula it is assumed that the coupling and propagation losses of the two modes of the sensor beam are different and are included in the amplitudes of the two modes.

The phase difference represented by the output signal varies with the absorption and desorption of chemical species on the surface of the waveguide. Because the formation of inclusion complexes is reversible, this invention can be used for substantially real-time sensing of targeted chemical agents. Sensitivity and specificity of the invention method and apparatus can be tuned by varying the size of the host reagent cavity and by selection of the chemical functionality of the host reagent molecules.

The output signal of the photodetector is transmitted to a phase sensitive detector, such as a lock-in amplifier, where the output signal of the photodetector is compared with a reference signal from the laser light source. The reference signal has the same modes and frequencies as the sensor beam and produces a reference interference signal having a beat frequency equal to the difference in frequency between the two modes of the reference beam. The reference signal has a phase equal to the optical phase difference between the orthogonally polarized light modes generated by the laser.

The phase of the beat frequency of the sensor beam (relative to the beat frequency of the reference signal) depends upon the optical phase difference between the two collinear, orthogonally polarized frequencies. The optical phase difference is caused by the changes in refractive index of the thin film host reagent that occur when the host reagent forms inclusion complexes with molecules of the targeted chemicals.

The phase sensitive detector produces an output signal which represents the relative phase difference between the reference signal and the sensor signal. The output signal can be stated as:

where $\Delta$ = change
$\Phi$ = phase
$\alpha$ = is proportional to
$\gamma_0$ = the vacuum wavelength of light
$N_v$ = effective refractive index of vertically polarized light
$N_H$ = effective refractive index of horizontally polarized light
L = length of the waveguide Another way of practicing the invention, without use of an independent reference signal from the laser light source, is to provide a reference signal by using one or more uncoated channels on a waveguide structure with a plurality of channels as reference channels. Alternatively, two modes of a laser beam can be used by splitting the two modes of the laser beam, sending one mode down a reference channel on a waveguide with a plurality of channels and the second mode down another channel on the same waveguide with a species-selective thin film of host reagent. The modes are then recombined and compared to the reference signal generated by the laser light source.

Figure 1:
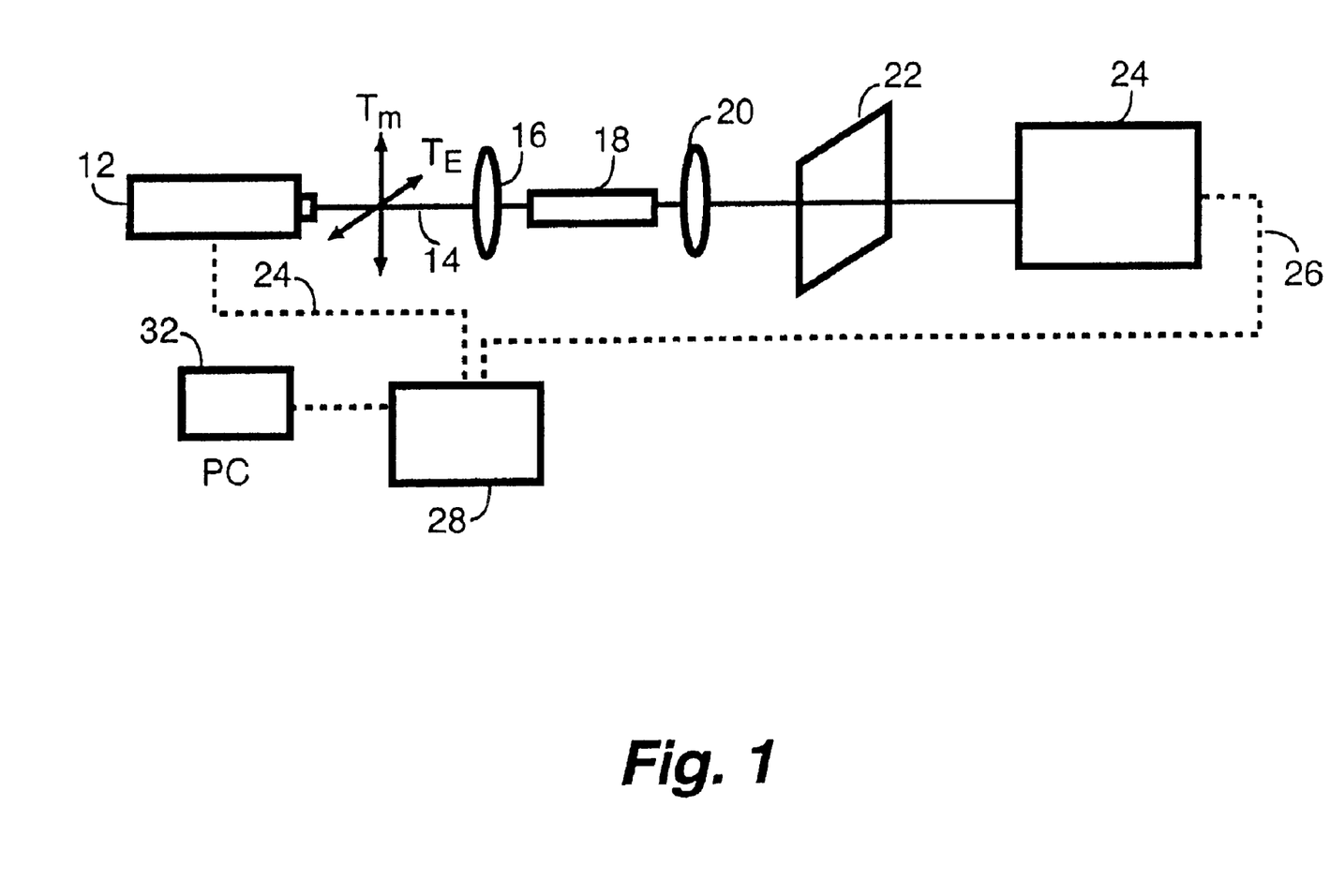
FIG. 1 is a schematic diagram of an example of an invention apparatus set up.

An example of a typical invention set up is shown in the schematic of FIG. 1. A laser 12 is adjusted to produce a beam of light 14 having two collinear, orthogonally polarized modes, as shown by the $T_M$ and $T_E$ arrows on the schematic. The two modes have different frequencies. The beam 14 is directed through a focusing lens 16 into a waveguide 18 that has attached thereto at least one thin film of the selected host reagent on the surface of the waveguide 18.

Light that propagates through the waveguide 18 is focused through another lens into a light polarizing analyzer 22 or other equipment for changing the light that comes from the waveguide 18 back to one polarization mode with one signal out of phase with the other signal. The transmission axis of the light polarizing analyzer 22 is oriented at an angle of 45° with respect to the axis of polarization of the two modes of light. The orthogonally polarized modes of the beam interfere at the photodetector 24.

The light polarizing analyzer 22 transmits a portion of each of the modes of light so that the signal from the polarizing analyzer 22 has some component of each of the modes.

Output of the light polarizing analyzer 22 is directed into a photodetector 24 such as a photodiode or photomultiplier. The photodetector 24 converts photons of light from the light polarizing analyzer 22 into electrical signals.

Output from the photodetector 24 is a sine wave conducted by way of an electrical connection 26 into a phase sensitive detector 28 such as a lock-in amplifier which compares the phase of the photodetector output with that of a reference signal supplied by the laser 12 or other light source by way of electrical connection 34 from the laser 12 or other light source to the phase sensitive detector 28.

The phase sensitive detector 28 detects and measures the relative phase between the external beat frequency reference signal and the beat frequency on the photodetector.

The measured phase difference between the output of the photodetector and the reference signal is proportional to the changes in the effective refractive indices of the modes of orthogonally polarized light.

A PC 32 is used to collect and display phase differences between signals from the phase sensitive detector 28 and the laser reference signal.

The two collinear, orthogonally polarized frequencies of light can be generated by any suitable source. A convenient light source is any laser which can generate a light beam having two orthogonally polarized light modes which are slightly offset in frequency. Presently preferred are Zeeman effect gas lasers, and more particularly, HeNe gas lasers, because these lasers can produce a beam of light with two orthogonally disposed frequencies in a range of wavelengths which can be transmitted by convenient waveguide materials.

When it is desired to have a smaller light source, a laser diode can be used to produce a beam which is then split into two beams having two frequencies and orthogonal polarization using a polarized beam splitter and modulator.

It is generally preferred to operate the laser in continuous mode, although long duration pulses could be used. The laser or other light source is operated to produce any wavelength of light which can be transmitted with low optical loss by the waveguide material. Wavelengths in the range from about 632 nm to about 1.5 microns are generally considered most useful for the presently preferred waveguide materials.

Useful frequency differences include those which fall within the band width (frequency detection range) of the photodetector and phase sensitive detector used. Any difference in frequency that is measurable with adequate signal to noise ratios can be employed.

Presently most preferred for use with the presently preferred waveguide materials are orthogonally polarized modes of laser light beam that differ by about 250 KHz in frequency and by about $3.3 \times 10^{-7}$ nm in wavelength.

The two orthogonally polarized mode beams ($T_E$ and $T_M$) are lens coupled into the leading end of one or more of the channels in the waveguide. The effective refractive index of each of the two modes is different due to the different polarization of the modes and the effective refractive index of each of the two modes is changed by selective inclusion of targeted chemical species in the thin film host reagent layer on the waveguide surface.

Waveguide sizes and configurations can vary greatly, depending upon the materials used, the wavelength at which the laser is operated, whether a laser or laser diodes are used as the laser light source and the type and thickness of the species-selective thin film host reagent.

Figure 2:
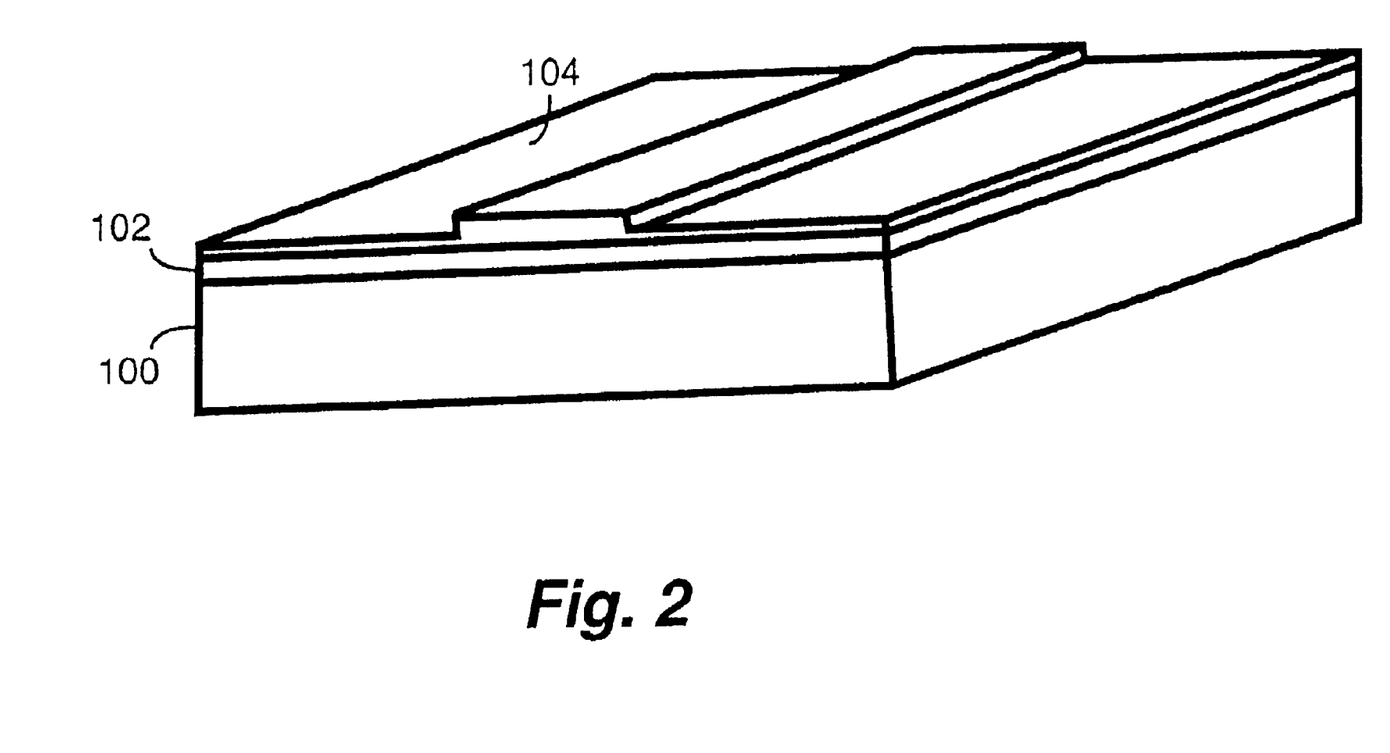
FIG. 2 is a schematic of a cross section of a single ribbed channel in an optical waveguide.

The waveguide may simply be a layer of waveguide material on a waveguide substrate as shown in FIG. 2. The thin film of host reagent 104 is bonded onto the surface of waveguide material 102 opposite the surface which is bonded to a waveguide substrate 100.

Figure 3:
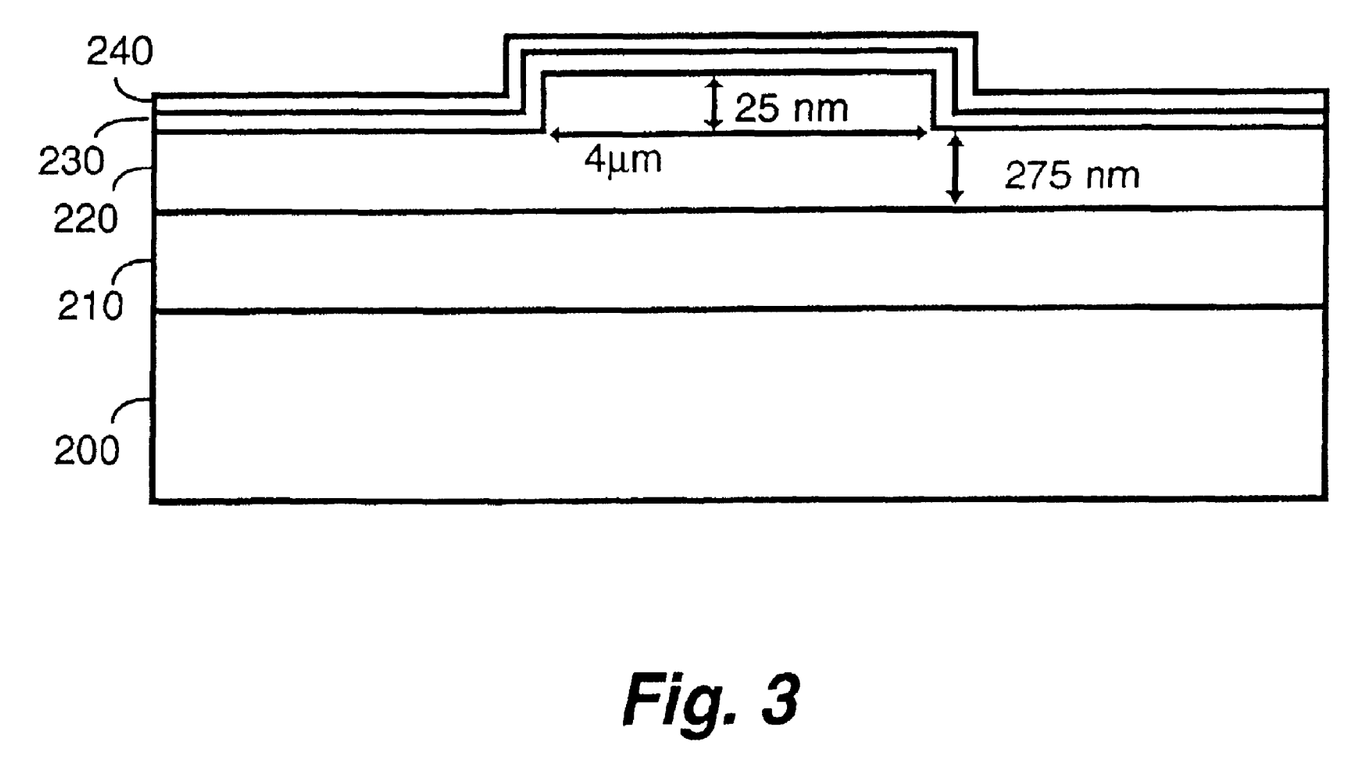
FIG. 3 is a schematic of a cross section of a ribbed channel waveguide with a coating layer.

However, waveguides more typically are a series of layers built up on a silicon chip or wafer as depicted schematically in FIG. 3. The silicon wafer or chip or other material that can be used serves as a waveguide substrate support 200. The waveguide substrate 210 is layered onto the waveguide substrate support 200 beneath the layer of waveguide material 220.

If desired, to provide a surface which facilitates bonding of the host reagent layer 240 to the waveguide, a thin waveguide material coating 230 can be applied by any suitable means to the waveguide material 220 surface. The two modes of laser light are guided through the high refractive index waveguide material 220 by the low refractive index waveguide substrate material 210 on one side and either the low refractive index species-selective thin film host reagent or waveguide coating 230 (waveguide attachment layer) on the opposite side of the layer of waveguide material 220.

Materials which are useful for the waveguide material are those which have high refractive indices, low light absorption, and which can be configured into very thin layers. The difference between the refractive index of the waveguide material and the refractive index of the substrate is more important than the refractive index of the waveguide material. The difference in refractive indices should be in the range from about 0.01 to about 1.0. More preferably, the difference between the refractive index of the waveguide material and that of the substrate is in the range from about 0.3 to about 0.5 since this difference can produce a small enough waveguide mode size in a vertical direction. The small mode size in vertical direction is important in increasing the sensitivity of the apparatus. This range of index of refraction differences is easily achieved with modem thin film deposition techniques.

Waveguide materials with refractive indices in the range from about 1.4 to about 3.5 are generally most useful in the invention, depending upon choice of substrate and refractive index of the thin film host reagent material.

Light absorption capacity of less than about 5 dB/cm is needed for operation of the invention. Light absorption capacity in the range from about 0.01 dB/cm to about 3 dB/cm is presently preferred because the lower waveguide losses result in higher output powers and thus longer waveguide lengths can be used. This increases the sensitivity.

Suitable waveguides generally need to be made from a material upon which the host reagent can be applied and a material which can be configured into very thin layers because thinner layers better concentrate the evanescent field.

Materials which can be used as waveguide material include, but are not limited to, silicon, silicon nitride, quartz, zinc oxide, zirconium oxide, tin oxide, indium-tin oxide, lithium niobate, gallium arsenide and titanium dioxide. Presently preferred is silicon nitride because the difference in indices of refraction when the silicon nitride is used with a silicon oxide or quartz substrate is about 0.5 and because high quality quartz substrates as well as silicon substrates with silicon oxide layers are commercially available and the deposition of silicon nitride films on these substrates is a well-established technology.

The waveguide material can be supported by a substrate of any material with a low index of refraction upon which the waveguide material with a high index of refraction can be deposited. Generally presently preferred waveguide substrate materials include, but are not limited to, silicon dioxide, silicate glass, quartz, gallium arsenide, lithium niobate and oxidized silicon.

Presently most preferred as waveguide substrate materials are quartz and oxidized silicon because they are compatible with modern microelectronics, are commercially available at reasonable prices, and because high index waveguide materials such as silicon nitride films can be easily deposited on these materials.

Alternatively, the high index waveguide material can be fabricated by diffusion of the waveguide material into the substrate. The diffusion technique can be used with titanium diffused in lithium niobate and ion exchange in silicate or borosilicate glasses.

Waveguides with at least one ribbed channel are useful because the channels confine light in the horizontal direction.

Figure 4:
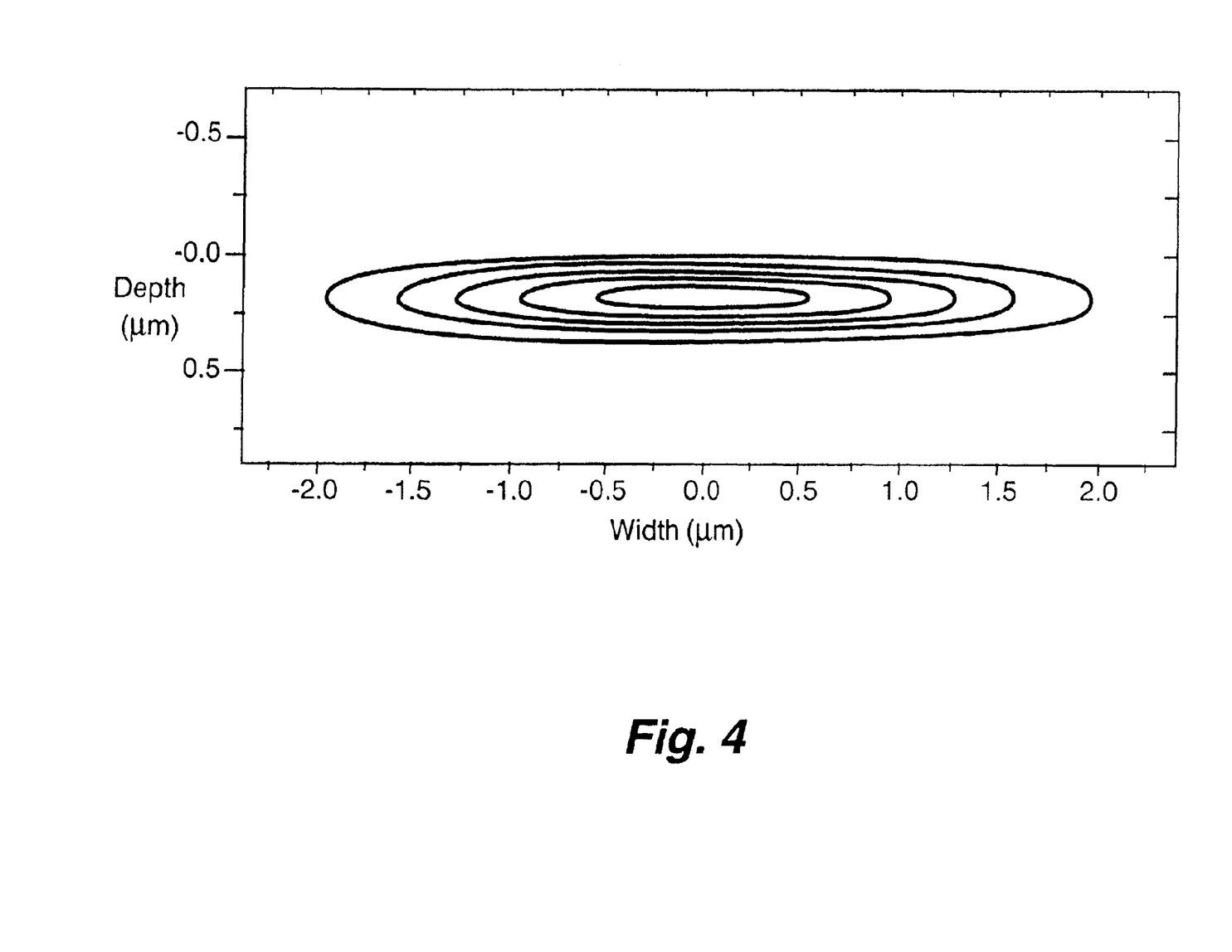
FIG. 4 is a graph of the optical power distribution for the ribbed optical waveguide shown in FIG. 3.

The high index silicon nitride channel waveguides offer tight vertical mode confinement which results in high sensitivity to changes in the optical characteristics of the host reagent layer. FIG. 4 is a graph of the optical power distribution for a 190 nm ribbed waveguide having a 275–300 nm silicon nitride waveguide, silicon dioxide waveguide coating, waveguide substrate and a silicon substrate support as shown in FIG. 3. Measurement was made with the top of the sensitive layer at a depth of 0 $\mu$m. Other power distributions can be used, depending upon the waveguide material thickness and refractive index.

Thin layers of high index waveguide material are generally preferable because the tight vertical mode confinement provides high sensitivity. Layers of waveguide material in the range from about 2 nm to about 1 micron can be used in the invention. Layers of waveguide material in the range from about 50 nanometers to about 10 microns, and more preferably, 275 to about 300 nanometers, in thickness are generally more suitable, depending upon the choice of material.

Waveguides with multiple channels (up to hundreds of channels) can be used to concurrently detect a plurality of chemical species or to provide reference channels so that use of a reference signal is unnecessary.

When some waveguide materials are used, serpentine channels with small bend radii can be used to increase the interaction length of the channel without increasing the outside dimensions of the planar waveguide structure.

An example of a typical waveguide construction (materials and dimensions) in accordance with the present invention is shown in the schematic of FIG. 3. In this example, a 1- to 3-micron thick base of oxidized silicon serves as the substrate 210 for a 275 to 300 nm thick layer of silicon nitride which serves as the waveguide material 220 and as a base for the very thin layer of waveguide coating 230 of silicon dioxide onto which the host reagent will be applied. As can be seen in FIG. 3, a sublayer 200 of a fourth material such as silicon (as in a chip or wafer) can be used as a support 200 for the silicon dioxide substrate 210, silicon nitride waveguide material 220, waveguide coating layer 230, and host reagent layer 240.

Materials which can be used for the species-selective or size-selective thin films of host reagent are cyclodextrin derivatives and calixarenes that form guest-host inclusion complexes with the molecules to be sensed. The thin film materials have "bucket-like" structures which are cavities in the molecular conformation. By adjusting the size and the chemical functionality of the cavities of the host reagents, highly specific recognition for selected molecules can be obtained.

Suitable cyclodextrin-derivative materials can be formed from materials including $\alpha$-cyclodextrin, $\beta$-cyclodextrin, $\gamma$-cyclodextrin or modified $\alpha$-cyclodextrins, $\beta$-cyclodextrins, or $\gamma$-cyclodextrins, preferably modified $\alpha$-cyclodextrins, $\beta$-cyclodextrins, or $\gamma$-cyclodextrins. Cyclodextrins are linked D-glucopyranose units with $\alpha$-cyclodextrin, $\beta$-cyclodextrin, $\gamma$-cyclodextrin being composed of 6, 7, or 8 units, respectively, with the units linked into a circular arrangement. Accordingly, the internal diameter of the cavities of each of $\alpha$-cyclodextrin, $\beta$-cyclodextrin, $\gamma$-cyclodextrin varies from the others. $\alpha$-cyclodextrin has a cavity size or internal diameter of about 4.7 to 5.2 Angstroms (Å), $\beta$-cyclodextrin has an internal diameter of about 6.0 to 6.5 Å, and $\gamma$-cyclodextrin has an internal diameter of about 7.5 to 8.5 Å.

The term "cyclodextrin derivative" refers to a cyclodextrin modified by the addition of other functional groups, e.g., a cyclodextrin wherein a functional group has been substituted for a hydrogen atom of one or more primary or secondary hydroxyl groups of the cyclodextrin. Functional groups can be any selected from a carboxyl group, a carboxyl alkyl group, a carboxylaryl group, an alkyl group, a hydroxyalkyl group, a sulfonic group, or an alkylenesulfonic group and the like or combinations thereof The alkyl group can be either a lower alkyl such as a one- to four-carbon alkyl group or a longer chain aliphatic containing from about 8 to about 22 carbons.

Modification of a cyclodextrin can alter the length and size of the internal cavity or alter the chemical compatibility or binding properties of the particular cyclodextrin derivative with a target chemical compound, or do both.

Cyclodextrin derivatives such as those described in U.S. Pat. No. 5,418,058 issued to Li and Swanson May 23, 1995, are generally suitable for use in the present invention.

Generally presently preferred cyclodextrin derivatives include, but are not limited to, peralkylated $\beta$-cyclodextrin, peralkylated $\gamma$-cyclodextrin, cyclodextrin derivatives containing aryl groups, and mixtures thereof. Presently most preferred are peralkylated $\beta$-cyclodextrin, peralkylated $\gamma$-cyclodextrin, heptakis(2-O-trimethylbenzyl)-$\beta$-cyclodextrin, octakis(2-O-trimethylbenzyl)-$\gamma$-cyclodextrin, heptakis(2-O-trimethoxylbenzyl)-$\beta$-cyclodextrin, octakis(2-O-trimethoxylbenzyl)-$\gamma$-cyclodextrin, and mixtures thereof Calixarenes which can be used in the invention are those which can be functionalized to permit attachment to the waveguide surface and which optimize binding to selected analytes. These include p-tert-butyl calix[n]arenes (with n=a number from 4 to 8) and their derivatives.

Generally presently preferred calixarenes include, but are not limited to, p-aryl-calix[n]arene, p-amino-calix[n]arene, p-alkyl-calix[n]arene and mixtures thereof. Presently most preferred are p-aryl-calix[4]arene, p-aryl-calix[6]arene, p-amino-calix[4]arene, p-amino-calix[6]arene, derivatives thereof and mixtures thereof.

Calixarene derivatives with substituents in the para position have deeper, larger cavities and thereby permit more control of binding to target analytes.

The highest sensitivity is achieved with thin films of host reagent material having high refractive indices that are sufficiently different from the refractive index of the waveguide material to prevent light loss from the waveguide during transmission.

The thin film of cyclodextrin derivative or calixarene host reagent material can generally include a single layer of the host reagent material or can include multiple layers of the host reagent material. Multiple layers can be preferred to enhance sensitivity of the selective thin film by providing additional inclusion sites. In multiple layers, a second layer of the host reagent material can be chemically bound upon bonding sites in the first layer of the host reagent material. There is generally no limit to the number of layers that can be employed, although usually the number of layers will be from about 1 to about 10.

An amount of cyclodextrin derivative or calixarene sufficient to form the desired thickness and number of layers is needed.

Sufficient total film loading by weight of the selective thin film host reagent material upon the waveguide material is needed to provide adequate sensitivity to a chemical sensor. By using multiple layers, the total film loading can be increased and such larger loadings may be desired for some applications.

Generally, the thin films of host reagent material are from about 2 nanometers to about 1 micron in thickness. In one embodiment, a second layer of a host reagent may be spin cast upon an initial layer of the same or a different host reagent deposited in a self assembly technique. When such a spin casting approach is used, thicker layers of the host reagent may be formed with film thicknesses from about 0.1 microns to about 5 microns.

The cyclodextrin derivative or calixarene host reagents form inclusion complexes with the target molecules to be sensed because the molecule to be sensed fits inside the cavities of the host reagent and is chemically attracted to, or at least chemically compatible with, the cavities of the host reagent.

The species selective host reagent thin films are attached to the waveguides by any suitable means such as low pressure chemical vapor deposition, solution reaction, spin coating, covalent bonding with a linking agent, or solution spraying. Presently preferred are host reagent layers of solution grown films. Presently preferred is covalent bonding of the host reagent thin films to the waveguide material with silane linking agents. Suitable agents for linking cyclodextrin derivative materials to optical waveguides with oxide surface layers include, but are not limited to, silane linking agents such as 4-aminopropyltriethoxysilane, 3-aminopropyltriethoxysilane, 7-octenyltrichlorosilane, 6-hexenyltrichlorosilane, 11-bromoundecyltrichlorosilane, para(chloromethyl)phenyl trichlorosilane, (3-acryloxypropyl)trichlorosilane, (3-acryloxypropyl)trimethoxysilane, and mixtures thereof.

Figure 5:
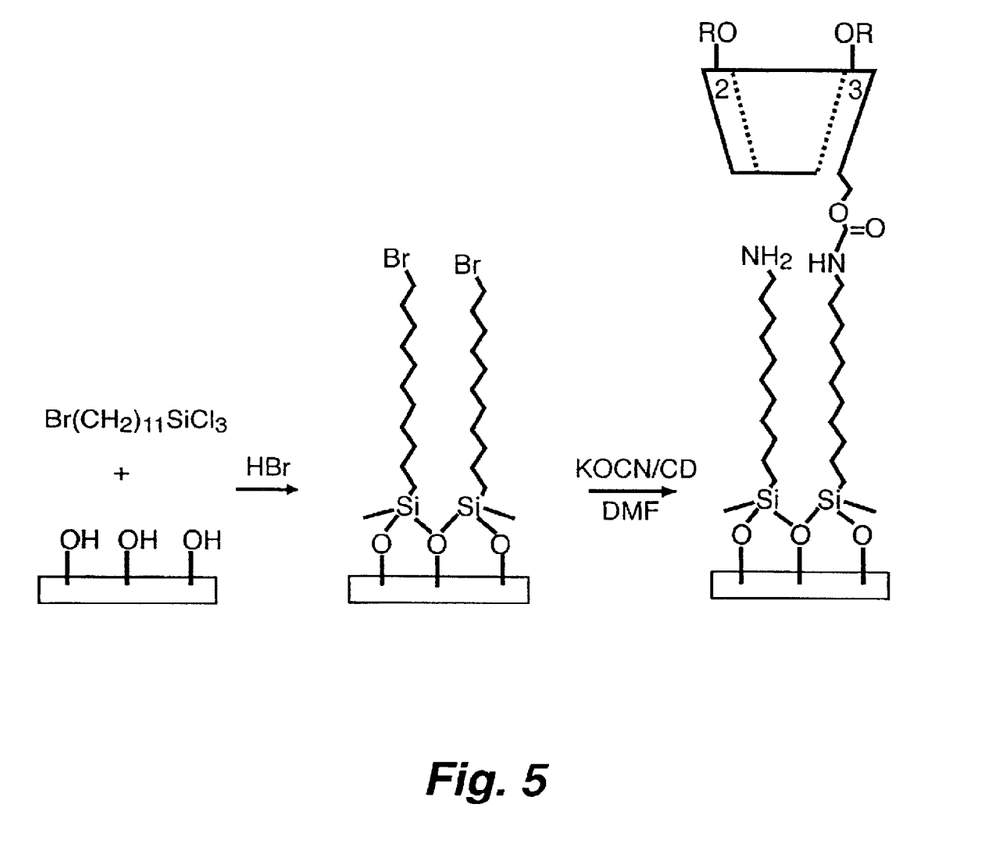
FIG. 5 is a schematic of a cyclodextrin derivative applied to an optical waveguide surface using a silane linking agent

Silanes such as 11-bromoundecyltrichlorosilane, 7-octenyltrichlorosilane and similar bifunctional silanes are particularly useful as linking agents because they can be used for self assembly of the cyclodextrin layer onto the waveguide material or waveguide material coating. FIG. 5 shows an example of how this can work.

The silane linking agent can be reacted initially with the oxide surface layer of the waveguide and then subsequently with the cyclodextrin derivative material or may be initially reacted with the cyclodextrin derivative material and then subsequently with the oxide surface layer of the oxide surface layer of the waveguide. After formation of the initial layer of cyclodextrin derivative material, a subsequent layer of the cyclodextrin derivative material can be linked through additional silane linking agents linked to a hydroxyl or other suitable functionality of the first cyclodextrin derivative material layer.

Alternatively, a subsequent layer of cyclodextrin derivative material can be linked directly to a hydroxyl or other suitable functionality of the first cyclodextrin derivative material layer without the silane linking agent.

Figure 6:
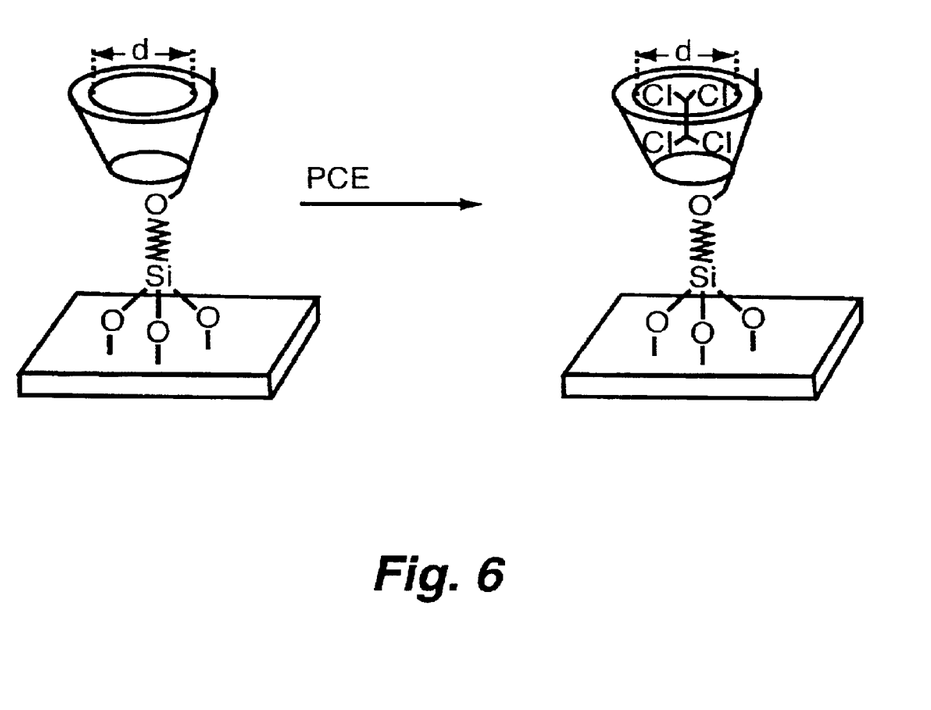
FIG. 6 is a schematic of a cyclodextrin derivative host reagent capture of a target molecule.

FIG. 6 shows a schematic of a cyclodextrin derivative typically used in practice of the invention shown relative to a waveguide surface. A primary hydroxyl group (O) has chemically attached through a silane linker to the oxide surface of the substrate, a secondary hydroxyl group has been reacted to form an ester group (OR) at the cavity of the host sensing reagent. The polar cavity of the cyclodextrin has a diameter from about 6.0 to about 6.5 angstroms, a secondary OR, and can attract and accommodate the targeted perchloroethylene molecule for inclusion. The polarization of the cavity enhances inclusion of the target analyte (PCE in this example).

Figure 7:
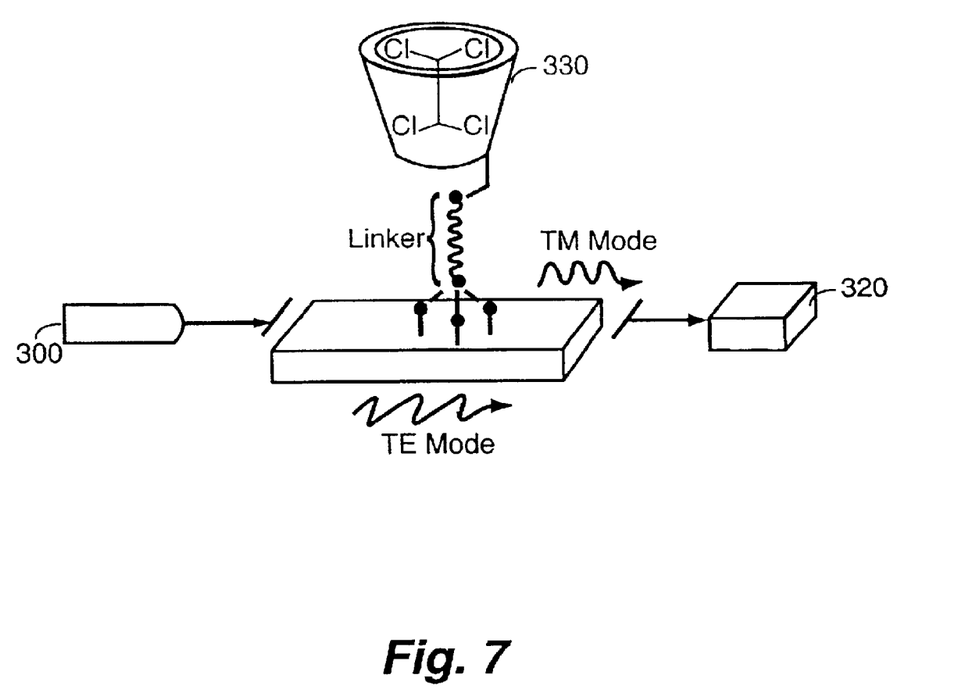
FIG. 7 is a schematic of a thin film of another cyclodextrin derivative covalently bound to an optical waveguide surface.

FIG. 7 shows a schematic of orientation relative to a waveguide surface. A laser 300 is positioned to direct a beam with $T_M$ and $T_E$ modes through a waveguide 310 into a detector 320. The waveguide 310 has an oxide surface to which the molecule of host reagent 330 is attached by a linker molecule to the cavity of the host reagent with inclusion of a targeted polychloroethylene molecule. Waveguide activity was calculated as: $1_{out} \sim 1 + \cos(\Phi_{TM} - \Phi_{TE})$.

Figure 8:
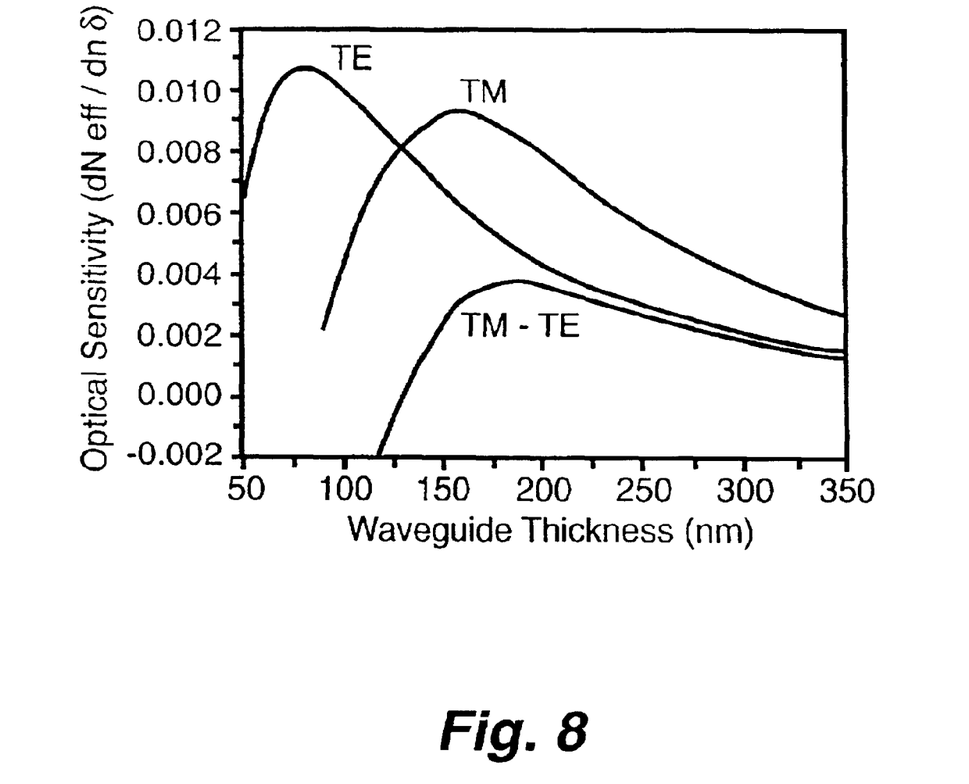
FIG. 8 is a graph of calculated optical sensitivity constants for $T_E$ and $T_M$ modes as a function of $Si_3N_4$ layer thickness.

FIG. 8 is a graph of calculated optical sensitivity constants for $T_E$ and $T_M$ modes as a function of $Si_3N_4$ layer thickness.

Figure 9:
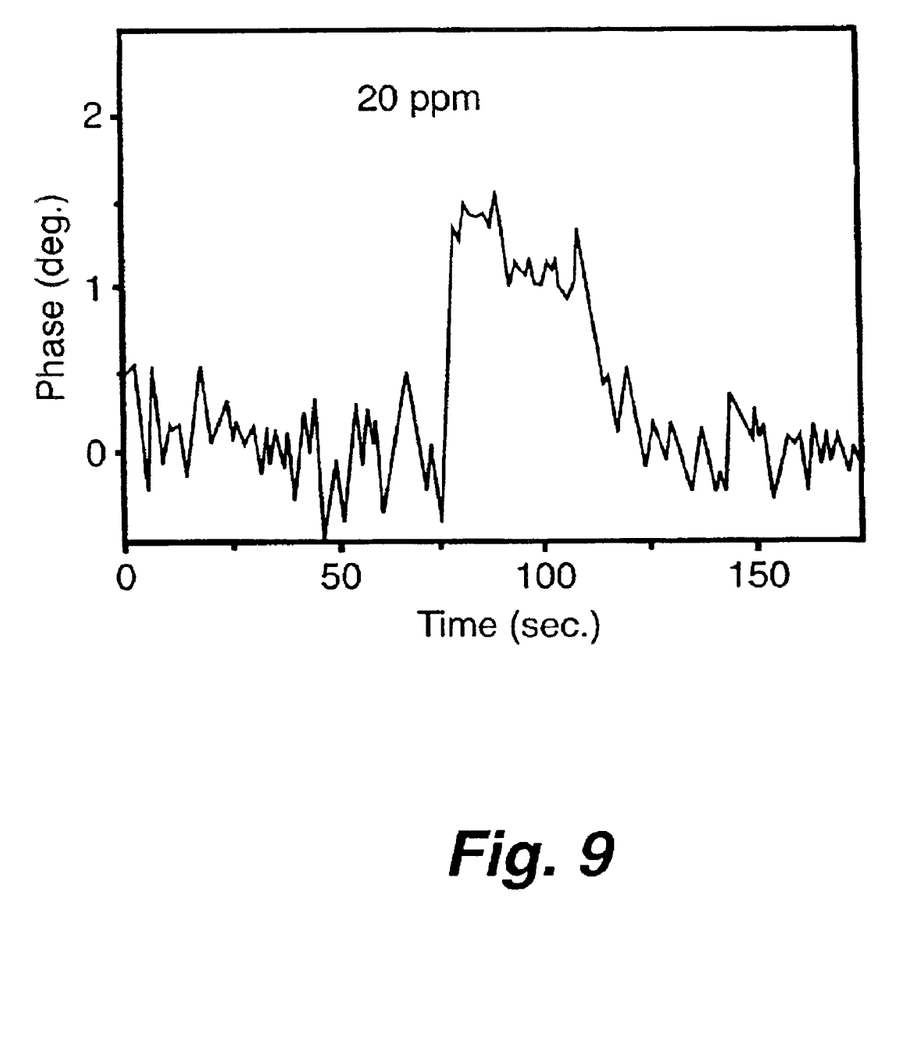
FIG. 9 is a graph of measured sensor response under exposure to 20 ppm toluene in air.

FIG. 9 is a graph of measured sensor response under exposure to 20 ppm toluene in air.

Figure 10:
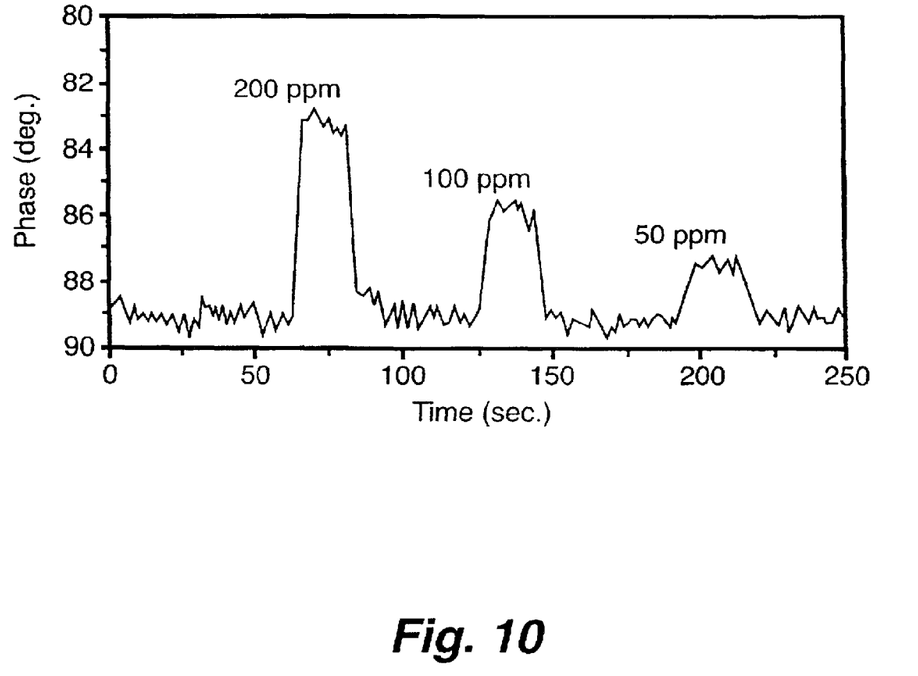
FIG. 10 is a graph of sensor phase response upon exposure to three different concentrations (200 ppm, 100 ppm and 50 ppm) of toluene.

FIG. 10 is a graph of sensor phase response upon exposure to three different concentrations of toluene. A wave guide in accordance with the invention was contacted with successive samples containing 200 ppm, 100 ppm, and 50 ppm, resulting in the reading shown in this graph.

The invention device is calibrated by running known amounts of known target chemical species across the optical waveguide during operation for results that can be used as references for analyzing the results of tests for identifying and quantifying the target species in an air or other gas sample.

Sensor sensitivity can be tuned by varying the size of the host reagent cavity and by optimizing the chemical functionality of the host reagent molecules.

Sensitivity of the invention apparatus also can be further enhanced by increasing the length of the waveguide channels, minimizing the thin film layer thickness to maximize the differential effective index change of the two modes of.,the beam due to contact with chemical agents in the host reagent cavities, and by including reference channels to compensate for common mode environmental effects such as those due to changes in temperature or pressure.

The invention sensor response to presence of the targeted chemicals is rapid (a matter of seconds) and reversible, allowing for substantially real time monitoring of presence and amount of targeted chemicals. Substantially real-time and reversible response to toluene and other volatile organic compounds can be achieved with ppm level sensitivity using the invention apparatus and methods.

INDUSTRIAL APPLICABILITY

The invention method and apparatus can be used for detecting with specificity extremely low levels of particular chemical species, including volatile organics, in the present of large concentrations of interfering species. Compact sensor arrays of invention apparatuses can be tailored for a variety of civilian and military chemical sensing applications.

What is claimed is:

1. An apparatus for chemical sensing comprising:
   (a) a waveguide sensor comprising a single mode waveguide and a selective thin film chemically bound upon at least some of said waveguide, said selective thin film comprising reagent capable of binding to chemical compounds;
   (b) a laser for providing a laser light beam comprising a first mode comprising a first frequency of light and a second mode comprising a second frequency of light, the first mode and second mode being substantially collinear and substantially orthogonal in polarization to each other, said laser positioned to direct said laser light beam into said waveguide;
   (c) a polarizer positioned to receive light output from said waveguide;

(d) a photodetector positioned to receive light output from said polarizer; and (e) a phase sensitive detector connected to said photodetector so as to receive signals from said polarizer.

2. An apparatus as recited in claim 1 wherein said laser is a Zeeman laser.

3. The apparatus as recited in claim 1 wherein said light source is a laser diode.

4. The apparatus as recited in claim 1 wherein said waveguide sensor comprises a planar waveguide.

5. The apparatus as recited in claim 4 wherein said planar waveguide is a ribbed channel waveguide.

6. The apparatus as recited in claim 1 wherein said waveguide sensor comprises a plurality of channels.

7. The apparatus as recited in claim 6 wherein said plurality of channels are serpentine channels.

8. The apparatus as recited in claim 1 wherein said waveguide comprises silicon, silicon nitride, quartz, zinc oxide, zirconium oxide, tin oxide, indium-tin oxide, lithium niobate, gallium arsenide or titanium dioxide.

9. The apparatus as recited in claim 1 wherein said waveguide comprises silicon nitride.

10. The apparatus as recited in claim 1 wherein said reagent comprises a cyclodextrin derivative.

11. The apparatus as recited in claim 1 wherein said reagent comprises a calixarene.

12. The apparatus as recited in claim 1 wherein said selective thin film comprises a plurality of layers of said reagent.

13. The apparatus as recited in claim 12 wherein said plurality of reagent layers comprises a first layer of cyclodextrin derivative attached to said waveguide and at least one other layer of cyclodextrin derivative attached to said first layer of cyclodextrin derivative.

14. The apparatus as recited in claim 12 wherein said first layer of cyclodextrin derivative and said at least one other layer of cyclodextrin derivative are different cyclodextrin derivatives.

15. The apparatus as recited in claim 1 wherein said selective thin film is about 2 nanometers to about 1 micron thick.

16. The apparatus as recited in claim 1 further comprising an oxide surface between said waveguide and said reagent.

17. The apparatus as recited in claim 16 wherein said oxide surface comprises silicon dioxide.

18. The apparatus as recited in claim 1 wherein said photodetector is a photodiode or photomultiplier.

19. The apparatus as recited in claim 1 wherein said phase sensitive detector is a lock-in amplifier.

20. The apparatus as recited in claim 1 further comprising a connection from said laser to said phase sensitive detector to transmit a reference signal.

21. The apparatus as recited in claim 6 wherein at least one of said plurality of channels is not coated with said thin film of reagent to provide a reference channel.

* * * * *